US00PP20770P2

(12) United States Plant Patent
Jandrew

(10) Patent No.: US PP20,770 P2
(45) Date of Patent: Feb. 23, 2010

(54) ***SCAVEOLA* PLANT NAMED 'BOMY LAVER'**

(50) Latin Name: *Scaveola aemula*
Varietal Denomination: Bomy Laver

(75) Inventor: Jason Jandrew, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/316,177

(22) Filed: Dec. 10, 2008

(51) Int. Cl.
*A01H 5/00* (2006.01)

(52) U.S. Cl. ..... Plt./363

(58) Field of Classification Search ..... Plt./363
See application file for complete search history.

*Primary Examiner*—Annette H Para
(74) *Attorney, Agent, or Firm*—S. Matthew Edwards

(57) ABSTRACT

A new *Scaveola* plant named 'Bomy Laver,' particularly distinguished by light purple-violet flower color, early and abundant flowering response, medium green foliage, initially semi-upright, becoming medium-compact and decumbent to trailing habit on a well-branched plant habit.

1 Drawing Sheet

Latin name of the genus and species of the plant claimed: *Scaveola aemula.*

Varietal denomination: 'Bomy Laver'.

BACKGROUND OF THE NEW PLANT

The present invention comprises a new *Scaveola*, botanically known as *Scaveola aemula*, and hereinafter referred to by the variety name 'Bomy Laver.'

'Bomy Laver' is a product of a planned breeding program. The new cultivar 'Bomy Laver' has light purple-violet flower color, early and abundant flowering response, medium green foliage, initially semi-upright, becoming medium-compact and decumbent to trailing habit on a well-branched plant habit.

'Bomy Laver' originated from a hybridization in a controlled breeding program in Gilroy, Calif. USA . The female parent was an unpatented, proprietary hybrid seedling identified as '1071-3' with blue color. '1071-3' has larger foliage, fewer branches, and less vigor than 'Bomy Laver.'

The male parent of 'Bomy Laver' was an unpatented, proprietary hybrid identified as '180' with violet color. '180' has darker color foliage, smaller flowers, and fewer branches than 'Bomy Laver.'

'Bomy Laver' was selected as one flowering plant within the progeny of the stated cross in May 2005 in a controlled environment in Gilroy, Calif. USA. The pollination took place in August 2004 and the seed sown in January 2005.

The first act of asexual reproduction of 'Bomy Laver' was accomplished when vegetative cuttings were taken from the initial selection in the May 2005 in a controlled environment in Gilroy, Calif. USA.

Horticultural examination of plants grown from cuttings of the plant initiated in May 2005 in Gilroy, Calif. USA, and continuing thereafter, has demonstrated that the combination of characteristics as herein disclosed for 'Bomy Laver' are firmly fixed and are retained through successive generations of asexual reproduction.

'Bomy Laver' has not been observed under all possible environmental conditions. The phenotype may vary significantly with variations in environment such as temperature, light intensity and day length.

A Plant Breeder's Right for this cultivar was applied for in Canada on Dec. 24, 2007. 'Bomy Laver' has not been made publicly available more than one year prior to the filing of this application.

DESCRIPTION OF THE DRAWINGS

The accompanying photographic drawing shows typical flower and foliage characteristics of 'Bomy Laver' with colors being as true as possible with an illustration of this type. The photographic drawing shows 3 flowering potted plants of the new variety in a basket and a close-up of the flowers. These plants were grown and photographed in Gilroy, Calif. USA in September 2007. These plants were approximately 3–4 months old.

DETAILED BOTANICAL DESCRIPTION

The measurements were taken on plants growing in Gilroy, Calif. USA in April 2008. The plants were growing in 4 inch pots in a greenhouse trial. These plants were about 3 months old.

Color Chart used: Royal Horticultural Society Colour Chart (R.H.S.) 2001

BRIEF SUMMARY OF INVENTION

The following observations, measurements, and comparisons describe plants grown Gilroy, Calif. USA. The following traits have been repeatedly observed and are determined to be basic characteristics of the new variety. The combination of these characteristics distinguishes this *Scaveola* as a new and distinct variety.

TABLE 1

DIFFERENCES BETWEEN THE NEW CULTIVAR 'BOMY LAVER' AND A SIMILAR VARIETY

| | 'Bomy Layer' | 'Pink Fanfare' (Patent status unknown) |
|---|---|---|
| Foliage color | Lighter | Darker |
| Branching | More branching | Fewer branches |
| Plant habit | Less upright | More upright |

Plant:

*Form, growth and habit.*—Initially semi-upright, becoming medium-compact and decumbent to trailing habit on a well-branched plant habit with medium green foliage.

*Plant height* (*inflorescence included*).—16–20 cm.

*Plant width.*—30–45 cm.

Foliage:

*Immature, leaf color, upper surface.*—RHS 146A.

*Lower surface.*—RHS 146B.

*Mature, leaf color, upper surface.*—Darker than RHS 146A.

*Lower surface.*—RHS 146B.

*Length.*—4.5–4.9 cm.

*Width.*—1.7–1.9 cm.

*Shape.*—Obolate.

*Base shape.*—Attenuate.

*Apex shape.*—Acute.

*Margin.*—Dentate.

*Texture, upper surface.*—Pilose.

*Texture, lower surface.*—Pilose mainly on the veins and margins.

*Color of veins, upper surface.*—RHS 144A basally; becoming indistinct otherwise.

*Color of veins, lower surface.*—RHS 144A basally; becoming indistinct otherwise.

*Petioles color.*—RHS 144A.

*Petioles length.*—2.0–2.5 cm.

*Diameter of petiole.*—0.3–0.35 cm.

*Texture.*—Pilose.

Stem:

*Number of main branches per plant.*—5–7.

*Number of leaves per stem.*—7–10.

*Color of stem.*—RHS 144A base color; overlaid with hints of anthocynanins in hues of about RHS 176B.

*Length of stem.*—25–28 cm.

*Diameter.*—0.3–0.4 cm.

*Length of internodes.*—1.0–4.0 cm.

*Texture.*—Slightly pilose.

*Color of peduncle.*—RHS 144A base color; overlaid with hints of anthocyanins in hues of about RHS 176B.

*Length of peduncle.*—13–15 cm.

*Peduncle diameter.*—0.2 cm.

*Texture.*—Slightly pilose.

Inflorescence:

*Type.*—Solitary flowers arise from the leaf axils with one flower per leaf axil in an alternate arrangement but appearing so close together they appear to be cluster like. Flowers are sessile.

*Number of flowers per inflorescence.*—Usually 7–10 open at a time.

*Duration of flowering.*—Continuous flowering throughout the Summer.

*Fragrance*—None.

*Lastingness of individual florets.*—6–8 days.

Bud (just before opening):

*Color.*—RHS 144C overlaid with a hint of RHS N77B.

*Length.*—2.1–2.3 cm.

*Width.*—0.3 cm at the widest portion.

*Shape.*—Broadly acicular.

Corolla:

*Form.*—Composed of 5 petals fused at the base and in a semicircular or fan-like arrangement to form a lower part which is open tube-shaped; the petals are situated at obtuse angles to the flower base and slightly overlap.

*Immature flower color, upper surface.*—RHS N82C base color; RHS 85C margins; RHS 83C longitudinal striations; RHS 155C and 144A rounded blotches basally; the inner 2 petals have a RHS 5A bar in the blotch; the outer 4 petals have a stripe of RHS N79A at the base.

*Lower surface.*—RHS N82C; RHS 85C margins.

*Mature flower color, upper surface.*—RHS 85A base color; RHS 84D margins; RHS 83C longitudinal striations; RHS 155C and 144A rounded blotches basally; the inner 2 petals have a RHS 5A bar in the blotch; the outer 4 petals have a stripe of RHS N79A at the base.

*Lower surface.*—RHS 85C; RHS 85C margins; RHS 155A basally.

*Floret diameter.*—3.4–3.6 cm.

*Floret length.*—3.6–3.8 cm.

*Petal length.*—1.6–1.8 cm.

*Petal width.*—0.6–0.7 cm.

*Petal shape.*—Elliptical.

*Apex shape.*—Cuspidate.

*Margin.*—Entire.

*Petal texture, upper surface.*—Papillose.

*Lower surface.*—Pilose on the midvein.

*Corolla color, inside.*—RHS 5A; RHS N79A striations.

*Outside.*—RHS 144C.

*Corolla length.*—1.6–1.7 cm.

*Corolla width.*—0.3–0.4 cm.

*Corolla texture, inside.*—Pilose.

*Outside.*—Pilose.

Sepals:

*Type.*—Composed of one larger and somewhat fleshy sepal and two narrow sepals, fused at the base.

*Color of sepals.*—RHS 144A.

*Length of sepals.*—0.3–1.0 cm.

*Width of sepals.*—0.1–0.3 cm.

*Sepal shape.*—Lanceolate.

*Apex shape.*—Acute.

*Margin.*—Entire.

*Texture, upper surface.*—Pilose.

*Lower surface.*—Glabrous.

Reproductive organs:

*Pistil.*—1.

*Length.*—1.6–1.7 cm.

*Style color.*—RHS 155B overlaid very lightly with RHS 183D.

*Stigma color.*—RHS 146D.

*Stigma texture.*—Villous hairs the color of RHS 183B.

*Stamens.*—5.

*Color of filaments.*—RHS 155B.

*Length of filaments.*—0.7 cm.

*Anther color.*—RHS 155A.

*Anther length.*—0.2 cm.

*Color of pollen.*—RHS 155B.

*Pollen amount.*—Moderate.

*Fertility/seed set.*—Not observed on this hybrid.

Disease/pest resistance: Disease resistance or susceptibility has not been observed on this hybrid.

What is claimed is:

1. A new and distinct variety of *Scaveola* plant named 'Bomy Laver,' substantially as illustrated and described herein.

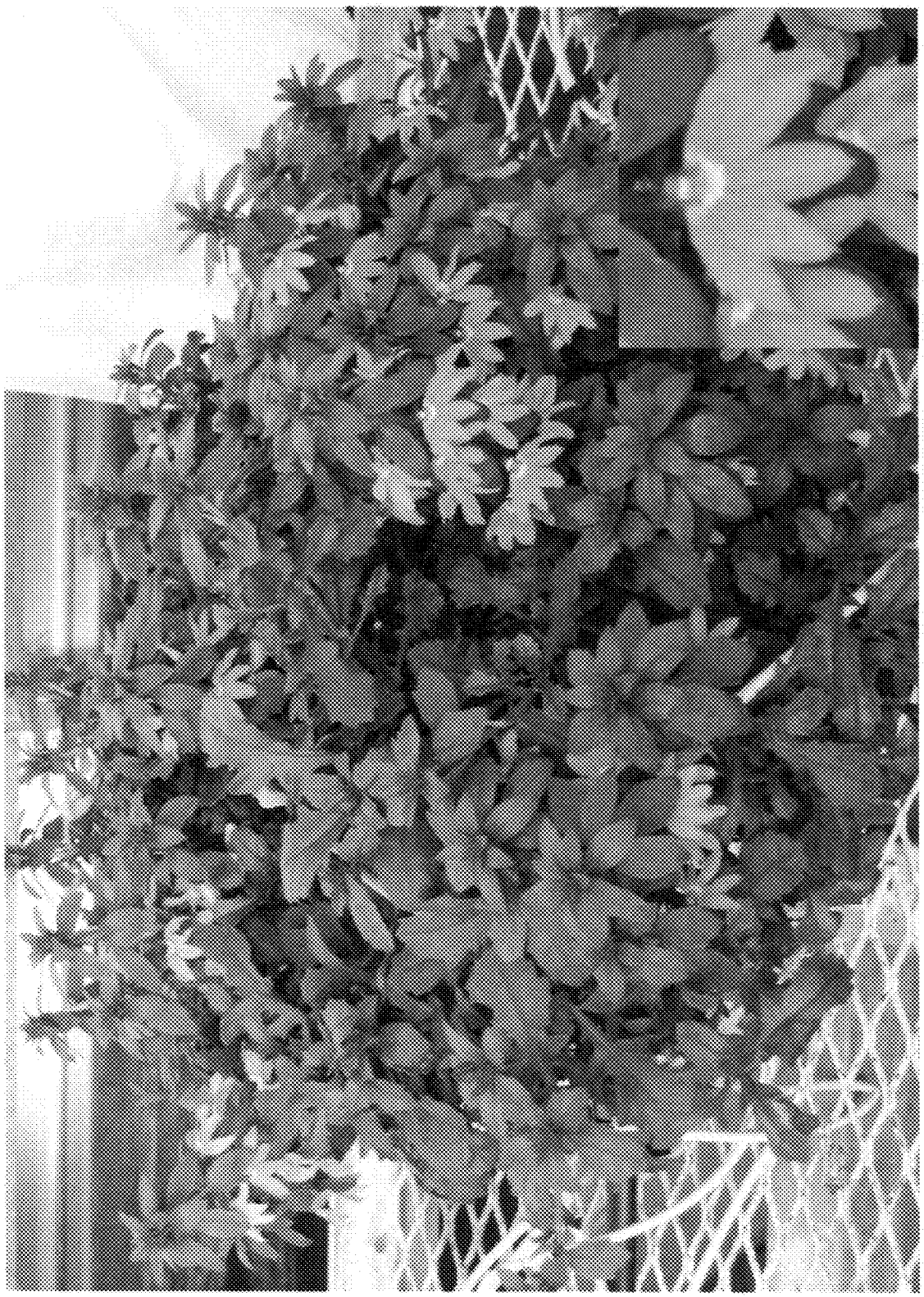

* * * * *